(12) United States Patent  
Ujihara et al.

(10) Patent No.: US 6,544,284 B1  
(45) Date of Patent: Apr. 8, 2003

(54) SHEET-FORM PACK AND METHOD OF PRODUCTION THEREOF AND METHOD OF USE THEREOF

(75) Inventors: Kazunari Ujihara, Tokyo (JP); Masato Saito, Kanagawa (JP); Eiji Hashida, Kanagawa (JP)

(73) Assignee: Kanebo Ltd., Tokyo (JP)

( * ) Notice: Subject to any disclaimer, the term of this patent is extended or adjusted under 35 U.S.C. 154(b) by 0 days.

(21) Appl. No.: 09/743,842

(22) PCT Filed: Jul. 22, 1999

(86) PCT No.: PCT/JP99/03903

§ 371 (c)(1),  
(2), (4) Date: Mar. 12, 2001

(87) PCT Pub. No.: WO00/04869

PCT Pub. Date: Feb. 3, 2000

(30) Foreign Application Priority Data

Jul. 23, 1998 (JP) ............................................. 10-207569

(51) Int. Cl.[7] ................................................. A61F 7/00
(52) U.S. Cl. ....................................................... 607/109
(58) Field of Search ................................ 132/319, 200; 604/303; 607/109, 110, 108; 602/8, 74

(56) References Cited

U.S. PATENT DOCUMENTS

| 194,815 | A | * | 9/1877 | Emerson-French | .......... 132/319 |
| 2,705,952 | A | * | 4/1955 | Becker | .......... 606/303 |
| 3,297,034 | A | * | 1/1967 | Peavy | .......... 607/108 |
| 4,397,701 | A | * | 8/1983 | Johnson et al. | .......... 156/62 |
| 4,559,047 | A | * | 12/1985 | Kapralis et al. | .......... 607/108 |
| 4,748,974 | A | * | 6/1988 | Richter et al. | .......... 602/8 |
| 5,176,621 | A | * | 1/1993 | Schulz | .......... 602/8 |
| 5,382,445 | A | * | 1/1995 | Yasis | .......... 602/8 |
| 5,879,378 | A | * | 3/1999 | Usui | .......... 607/108 |
| 5,972,325 | A | * | 10/1999 | Rachman | .......... 607/109 |

* cited by examiner

Primary Examiner—Todd E. Manahan  
(74) Attorney, Agent, or Firm—Hogan & Hartson, LLP

(57) ABSTRACT

A sheet-like pack includes a plurality of sheets, each of the sheets laid one upon another and cut into a predetermined shape. Each of the sheets includes gypsum and a sheet-like substrate impregnated with said gypsum. The sheet-like pack also includes an insulating sheet laid on a top surface of the plurality of sheets. A thermal pack is obtained by impregnating the sheet-like pack with water, applying the sheet-like pack on a predetermined portion where a cosmetic composition is applied, and removing the sheet-like pack solidified after a lapse of a predetermined time.

9 Claims, 2 Drawing Sheets

SHEET-FORM PACK AND METHOD OF PRODUCTION THEREOF AND METHOD OF USE THEREOF

TECHNICAL FIELD

The present invention relates to a sheet-like pack capable of obtaining a beautifying effect by applying on the face, body or the like, and its production and use.

BACKGROUND ART

Various cosmetologies capable of exerting a beautifying effect have hitherto been employed in esthetic salons. Particularly, with respect to a pack to be applied on the face, body or the like, a large number of techniques capable of exerting an effect of removing stain on the skin and an effect of firming the skin have been suggested. Among these techniques, a thermal pack for generating heat by applying gypsum on the skin has become very popular because of its significant effect of beautifying the skin and firming the flabby skin as well as relaxing effect of making persons comfortable.

However, a conventional thermal pack was not necessarily satisfactorily in view of convenience because water is mixed with gypsum immediately before applying on the skin. That is, the thermal pack had a drawback that gypsum is immediately solidified when it is not mixed with water immediately before applying on the skin, thereby making it difficult to smoothly apply on the skin. Also it has a drawback that considerably skilled art is required to apply gypsum dissolved in water on the uneven portion such as face or the like so that it is impossible for salesman to easily apply to subjects at a shop front where cosmetics are sold and for users to apply to themselves. Uniform application on the skin gives partial oppressive sensation and uniform heat generation. In some case, troubles such as low-temperature burn injury are likely to occur.

The present invention has been made in light of these circumstances and an object thereof is to provide a sheet-like pack, which can be applied on the face, body or the like very easily, thereby obtaining a proper thermal pack effect, and its production and use.

DISCLOSURE OF THE INVENTION

To attain the object described above, the sheet-like pack of the present invention has the following constitution. That is, it is a sheet-like pack comprising a plurality of sheets, which is obtained by laying said sheets one upon another and cutting into a predetermined shape, said sheet comprising gypsum and a sheet-like substrate impregnated with said gypsum. The sheet-like pack may be in a shape of the face.

The sheet-like pack of the present invention can be produced by impregnating a sheet-like substrate with a treating agent containing gypsum; subjecting to a heat treatment at a temperature within a range from 60 to 120° C.; laying a plurality of heat-treated sheets one upon another; and cutting into a predetermined shape.

The method of using the sheet-like pack of the present invention is characterized by impregnating a sheet-like pack with water, said sheet-like pack comprising a plurality of sheets, which is obtained by laying said sheets one upon another and cutting into a predetermined shape, said sheet comprising gypsum and a sheet-like substrate impregnated with said gypsum; applying said sheet-like pack on a predetermined portion where a cosmetic composition is applied; and removing said sheet-like pack solidified after a lapse of a predetermined time from said predetermined portion.

BEST MODE FOR CARRYING OUT THE INVENTION

The present invention will be described in detail with reference to the accompanying drawings.

Figure 1:
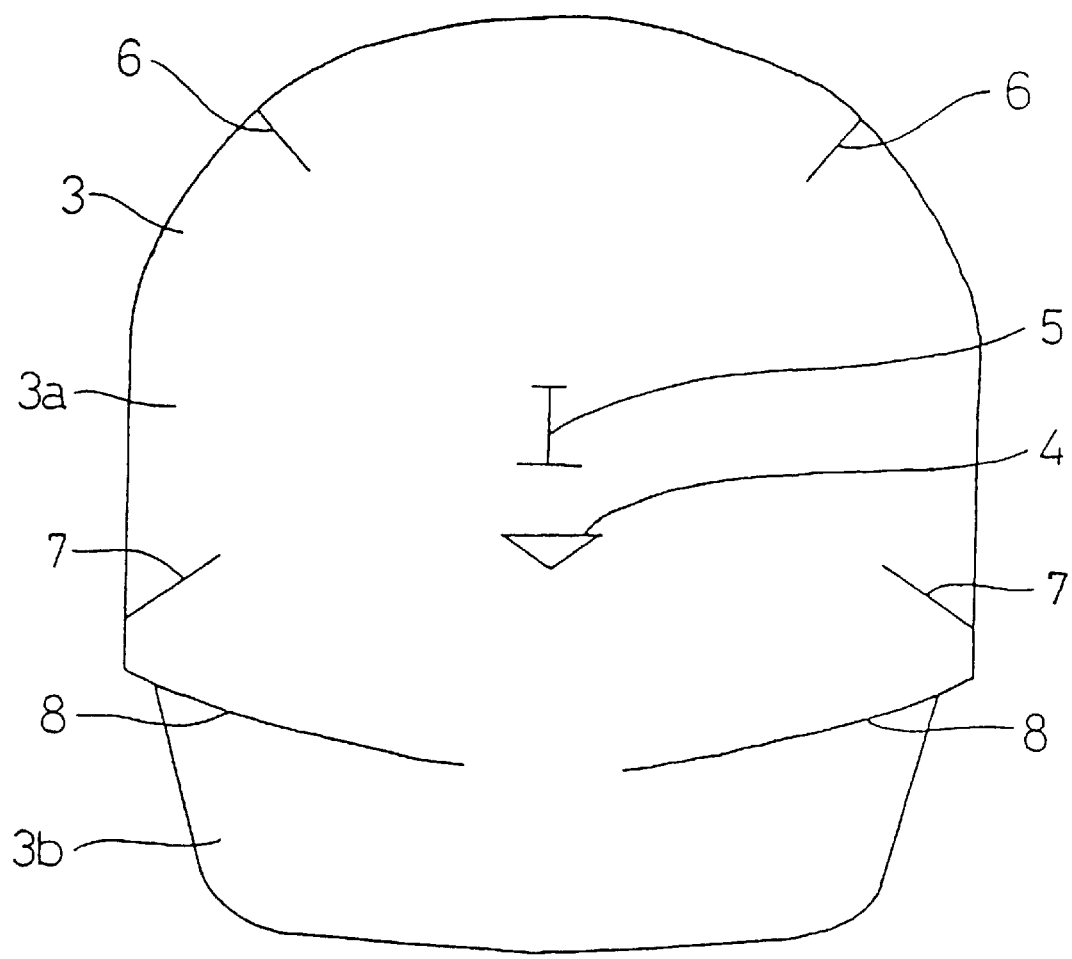
FIG. 1 is a front view of a preferable sheet-like pack according to the present invention.
Figure 2:
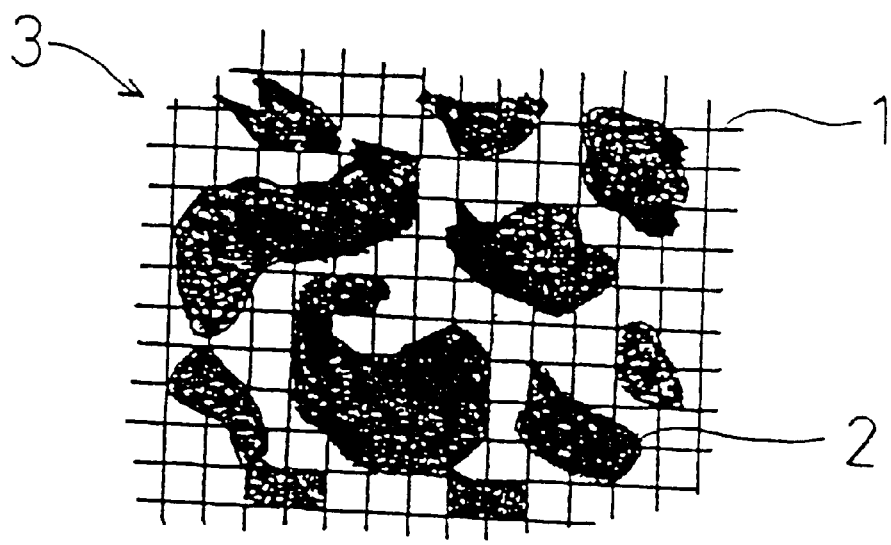
FIG. 2 is a schematic view for explaining a sheet used in the sheet-like pack.

FIG. 1 shows the form of a preferable sheet-like pack according to the present invention. This sheet-like pack is used in such as manner as to apply on the site ranging from the entire face to the cervical region and is obtained by forming a sheet (3), which is produced by uniformly impregnating a sheet-like substrate (1) made of a gauze with gypsum (2) to form a sheet (3), laying eight pieces of sheets (3) one upon another, and cutting into a shape of the face, as shown in FIG. 2. In this sheet-like pack, the portion (3a) corresponding to the face is formed into a shape of the face having a size of about 20 cm in a longitudinal direction and about 25 cm in a lateral direction and the portion corresponding to the mouth is provided with a hole (4) having a shape of inverted triangle and, furthermore, the portion corresponding to the nose is provided with a notch (5) having an I-shape. Also the portion corresponding to the forehead is provided with a pair of right and left notches (6) each having a length of about 2.5 cm and the portion corresponding to the cheeks is provided with a pair of right and left notches (7) each having a length of about 4.0 cm. Also the lower portion of the portion (3a) corresponding to the face is provided extendedly with the portion (3b) having an extended length of about 6 cm for applying on the cervical region via a pair of right and left notches (8) each having a length of about 10 cm. Both right and left ends of the portion (3b) for applying on the cervical region are formed backward from the portion (3a) corresponding to the face by about 1 cm.

The sheet-like substrate (1) is made of a gauze (degreased cotton cloth) of 100% cotton and the entire surface thereof is uniformly impregnated with gypsum (2) to form a piece of sheet (3) (see FIG. 2).

The sheet-like pack with such a constitution can be produced by impregnating a sheet-like substrate (1) with a treating agent containing gypsum (2), subjecting to a heat treatment at a temperature within a range from 60 to 120° C., laying eight pieces of dried sheets (3) one upon another, and cutting into a shape of the face.

As the gypsum (2), there can be used gypsum hemihydrate (calcined gypsum: $CaSO_4 \cdot \frac{1}{2}H_2O$) which causes the hydration reaction when kneaded with water, thereby to exhibit a setting action. First, a treating agent is prepared by adding a solvent such as methanol, water or the like, a binder, a viscous material and a viscosity modifier to the gypsum hemihydrate (2), and mixing them. After the treating agent is applied uniformly via a rotating roller while flowing continuously the gauze as the sheet-like substrate (1) having a predetermined width in one direction, the gauze is dried by subjecting to a heat treatment at a temperature ranging from about 60 to 120° C. while passing through a device for heat and drying treatment, and then taken up around a roller. When the temperature for heat treatment is lower than 60° C., gypsum (2) is not easy to dry. On the other hand, when the gauze is subjected to a heat treatment at a temperature higher than 120° C., anhydrous gypsum is produced. Therefore, the temperature for heat treatment is controlled within a range from 60 to 120° C.

Then, eight pieces of cut gauze sheets obtained by cutting the taken-up gauze into a predetermined size are laid one upon another and cut into a shape of the face. In case those obtained by impregnating the gauze as the sheet-like substrate (1) with gypsum (2) are cut into a shape of the face, eight pieces of the gauze cut sheets, which are obtained by previously cutting the gauze into a square shape of about 30 cm×about 30 cm in size, are preferably laid one upon another and cut by punching into a shape of the face. By punching into a shape of the face after putting the eight-layered gauze in a synthetic resin bag, scatter of gypsum (2) can be prevented, thereby improving the workability.

The sheet-pack thus formed is used in such a manner as to apply on the face and the cervical region after impregnating sufficiently with water. At this time, it is preferred that a cosmetic composition capable of exerting a desired beautifying effect (e.g. cream, etc.) is sufficiently applied on the face and the cervical region and, after covering the cast of eyes and cheeks with finely torn cotton impregnated with water and further covering the lips with finely torn cotton impregnated with water, the sheet-like pack softened by impregnating with water is positioned at a predetermined portion of the face and the cervical region and is contacted closely with the face and the cervical region while fitting the sheet-like pack with them. In case of fitting the sheet-like pack with the face, the sheet-like pack can be easily contacted closely with the face by using the respective notches (5), (6) and (7) described above. Since a deep notch (8) is provided between the portion (3a) corresponding to the face and the portion (3b) for applying on the cervical region, the sheet-like pack can be contacted closely with the cervical region, securely and easily. After a lapse of a predetermined time required to obtain a sufficient thermal pack effect (about 15 minutes in this form), the sheet-like pack solidified along the face and the cervical region is removed, thus obtaining a thermal pack effect capable of uniformly penetrating the cosmetic composition such as cream applied on the face and the cervical region into the skin and firming the flabby skin.

In case the sheet-like pack is impregnated with water, the sheet-like pack can be uniformly impregnated with a sufficient amount of water by charging water at 20–25° C. in a container in which the sheet-like pack can be dipped, and dipping the sheet-like pack therein. The thermal pack effect can be further improved by covering the face and the cervical region with the sheet-like pack and placing thereon an insulating vinyl sheet. The insulating vinyl sheet can also be placed on the face and the cervical region before covering them with the sheet-like pack. After the solidified sheet-like pack was removed, the skin is preferably conditioned by applying a lotion having a high moisture retention action.

Figure 3:
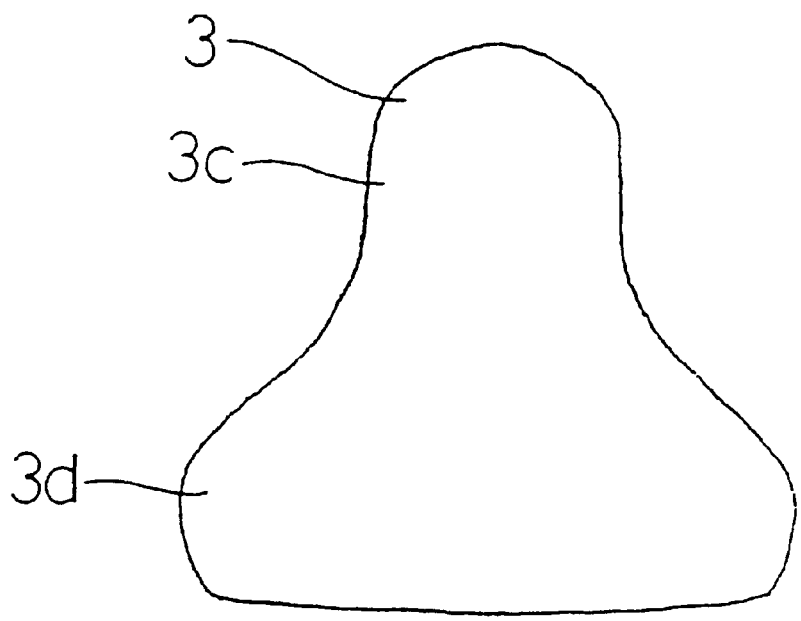
FIG. 3 is a front view showing another form of a sheet-like pack according to the present invention.

FIG. 3 shows another form of a sheet-like pack according to the present invention. This sheet-like pack is applied on the nose and is obtained by laying eight pieces of the same sheets (3) as those in the form described above one upon another and cutting into a shape which fits with that of the nose. The length in a longitudinal direction of the sheet-like pack thus formed is about 6.5 cm, the width of the upper narrow portion (3c) is about 3 cm, and the width of the lower large wide portion (3d) is about 7 cm. The sheet-like pack thus formed is capable of covering the entire nose in a state of being impregnated with water. It is possible to exert a sufficient thermal pack effect on the nose by impregnating this sheet-like pack with water, applying on the nose on which a cosmetic composition has been applied, contacting the sheet-like pack closely with the nose while fitting with it, and removing the solidified sheet-like pack after a lapse of a predetermined time (about 15 minutes in this form).

The sheet-like pack of the present invention can be applied as a partial pack for region under eyes and a pack for bodies such as hands, bust and the like, in addition to packs in two forms described above such as pack for face and pack for nose, by changing the cut shape. Also the exothermic temperature can be easily changed by changing the amount of gypsum or changing the number of pieces of sheets to be laid one upon another according to the application portions and subjects' taste. Accordingly, it is made possible to apply a thermal pack suited for the skin condition of the application portions and subjects' taste by preparing plural kinds of sheets having different amounts of gypsum, appropriately controlling the number of pieces of sheets to be laid one upon another, or changing the setting time. In two embodiments described above, various conditions are set so that heat generates gradually until the sensible temperature becomes about 40° C. and then the temperature gradually becomes lower.

Although the cotton 100% gauze was used as the sheet-like substrate in the embodiments described above, the sheet-like substrate is not limited thereto and the other sheet-like substrate can also be used as far as it can be easily impregnated with gypsum and applied on the skin by impregnating with water. It is preferred to select a material, which causes less discomfort to the skin and is easily contacted closely with the skin while fitting with it. For example, it is also preferred to use a nonwoven fabric. It is also possible to provide the sheet-like pack with flavor and color by adding perfumes and coloring pigments in the treating agent containing gypsum.

EXAMPLES

Using a gauze of 100% cotton as the sheet-like substrate (1), a treating agent, which was prepared by adding a solvent and a binder were respectively added in the proportion of about 60 and 5 based on 100 of gypsum hemihydrate, further adding a viscous material and a viscosity modifier and mixing them, was uniformly adhered on the gauze. The gauze was dried by subjecting to a heat treatment at about 100° C. and then cut into square shape of about 30 cm×about 30 cm in size. Eight pieces of cut-gauze sheets were laid one upon another, put in a vinyl bag, and then cut into a shape of the face in that state. The weight was about 240 g per eight pieces of sheets.

Using this sheet-like pack, ten female adults were actually subjected to a cosmetology. Concretely, a nutrient cream capable of exerting an effect of supplying water and oil was previously applied on the face and the skin of the cervical region of each person, and then the sheet-like pack was impregnated with water and applied and contacted closely with the face and the cervical region. After a lapse of about 15 minutes, the sheet-like pack was removed and we asked the persons about their impressions. As a result, we obtained such impressions as "comfortable", "the skin was moisturized" and "we feel the skin was firmed" from all ten persons. Also we obtained such opinion as "very convenient" from cosmologists.

INDUSTRIAL APPLICABILITY

As described above, according to the present invention, there can be provided a sheet-like pack, which can be applied on the face, body or the like very easily, thereby obtaining a proper thermal pack effect, and can also be used simply even by persons other than persons skilled in the art, and its production and use.

What is claimed is:

1. A sheet-like pack comprising:

a plurality of sheets, each of said sheets laid one upon another and cut into a predetermined shape, each of said sheets comprising gypsum and a sheet-like substrate impregnated with said gypsum; and an insulating sheet laid on a top surface of the plurality of sheets.

2. A sheet-like pack comprises a plurality of sheets, each of said sheets laid one upon another, each of said sheets comprising gypsum and a sheet-like substrate impregnated with said gypsum and each of said sheets being cut into a shape of the human face.

3. A method of producing the sheet-like pack of claim 1 or 2 comprising:

impregnating a sheet-like substrate with a treating agent containing gypsum;

subjecting to a heat treatment at a temperature within a range from 60 to 120° C. to produce a heat-treated sheet;

laying a plurality of said heat-treated sheets one upon another; and cutting each of said heat-treated sheets into a predetermined shape.

4. A method of using a sheet-like pack, which comprises the steps of:

impregnating a sheet-like pack with water, said sheet-like pack comprising a plurality of sheets, each of said sheets laid one upon another and cut into a predetermined shape, each of said sheets comprising gypsum and a sheet-like substrate impregnated with said gypsum;

applying said sheet-like pack on a predetermined portion where a cosmetic composition is applied; and removing said sheet-like pack solidified after a lapse of a predetermined time from said predetermined portion.

5. The sheet-like pack according to claim 4, wherein the sheet-like substrate is gauze.

6. The sheet-like pack according to claim 4, wherein the plurality of sheets totals eight sheets.

7. The sheet-like pack according to claim 4, wherein each the plurality of sheets is uiniformly impregnated with gypsum.

8. The sheet-like pack according to claim 4, wherein the predetermined portion is a human face.

9. The sheet-like pack according to claim 4, wherein the predetermined portion is a cervical region of a human body.

* * * * *